United States Patent [19]

Alper et al.

[11] Patent Number: 4,704,481

[45] Date of Patent: Nov. 3, 1987

[54] PROCESS FOR THE DESULPHURIZATION OF MERCAPTANS

[75] Inventors: Howard Alper, Ottawa, Canada; David J. H. Smith, Camberley,, England

[73] Assignee: The British Petroleum Company p.l.c., London, England

[21] Appl. No.: 823,486

[22] PCT Filed: May 23, 1985

[86] PCT No.: PCT/GB85/00221

§ 371 Date: Jan. 6, 1986

§ 102(e) Date: Jan. 6, 1986

[87] PCT Pub. No.: WO85/05354

PCT Pub. Date: Dec. 5, 1985

[30] Foreign Application Priority Data

May 24, 1984 [GB] United Kingdom ............... 8413371

[51] Int. Cl.$^4$ ............................................. C07C 41/00

[52] U.S. Cl. .................................. 568/658; 570/190; 585/469

[58] Field of Search .................. 570/190; 585/469; 568/658

[56] References Cited

PUBLICATIONS

Shim, Tetrahedron Letters, vol. 26, No. 16 (1985) 1935–1938.

Primary Examiner—Donald B. Moyer
Assistant Examiner—Joseph A. Boska
Attorney, Agent, or Firm—Brooks Haidt Haffner & Delahunty

[57] ABSTRACT

Benzylic and aromatic mercaptans are desulphurized by contacting the mercaptan with carbon monoxide at elevated temperatures in the presence of an aqueous hydrocarbon and a cobalt carbonyl catalyst.

7 Claims, No Drawings

PROCESS FOR THE DESULPHURIZATION OF MERCAPTANS

The present invention relates to a process for the desulphurisation of benzylic and aromatic mercaptans. More specially, this invention relates to the desulphurisation of benzylic and aromatic mercaptans in the presence of an aqueous hydrocarbon solvent and a cobalt carbonyl catalyst.

Because of the long-term potential availability of carbon monoxide, a vast amount of research has been directed in recent times towards its utilisation in chemicals syntheses. This concentration of effort has led to commercial processes for the production of acetic acid by the reaction of methanol and carbon monoxide, and to another process whereby acetic anhydride is produced by the reaction of methyl acetate and carbon monoxide. Many other materials, for example alkyl halides, are reported to react with carbon monoxide but the development of commercial processes based on these reactions is still in the formative stages.

Our European patent application No. 84308313.0 describes a process for the production of an ester having the formula $RCOOR^1$ by reacting at elevated temperature a mercaptan of formula RSH where R is a benzylic or aromatic moiety with carbon monoxide and an aqueous alcohol of formula $R^1OH$ in the presence as catalyst of a cobalt carbonyl.

We have now found that benzylic and aromatic mercaptans can be desulphurised by contacting the mercaptans with carbon monoxide at elevated temperature in the presence of an aqueous hydrocarbon solvent and a cobalt carbonyl catalyst.

Accordingly, the present invention provides a process for the desulphurisation of a mercaptan of the formula RSH wherein R is a benzylic or aromatic moiety which process comprises contacting the mercaptan with carbon monoxide at elevated temperature in the presence of an aqueous hydrocarbon solvent and as catalyst a cobalt carbonyl catalyst.

Within the context of the present application the term desulphurisation means the removal of sulphur to form the corresponding hydrocarbon. Thus application of the process of the invention to a p-methylbenzyl mercaptan results in the formation of p-xylene and from m-toluenethiol there is formed toluene.

In the formula RSH, R is either a benzylic or an aromatic moiety. The benzylic moiety is of general formula:

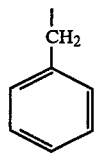

and may be substituted in the benzene nucleus portion thereof by, for example, hydrocarbyl groups such as by alkyl groups or by functional groups such as halide or alkoxy groups. Examples of benzylic mercaptans include but are not limited to p-methylbenzyl mercaptan, o-methylbenzyl mercaptan, p-methylbenzyl mercaptan, p-chlorobenzyl mercaptan, 2,4-dichlorobenzyl mercaptan and the like.

The aromatic moiety may be either substituted or unsubstituted and includes aryl, arylene and multiply substituted moieties. The substituted aromatic moiety may be substituted with, for example, alkyl, alkenyl or halide groups. Examples of aromatic mercaptans include but are not limited to m-toluenethiol, p-bromothiophenol, 2-naphthene thiol, phenylthiol and the like. Mixtures of aromatic mercaptans and benzylic mercaptans can be desulphurised by the process of the present invention.

Carbon monoxide may be obtained from a wide variety of carbonaceous sources using well-established conversion technology. The carbon monoxide may be pure or may contain such impurities as carbon dioxide, nitrogen or hydrogen. The carbon monoxide pressure may suitably be the autogenous pressure at the reaction temperature employed. Alternatively, carbon monoxide pressures in excess of the autogenous pressure, for example from 2 to 250 psig above the autogenous pressure, may suitably be employed.

As the hydrocarbon solvent, either an aromatic or an aliphatic liquid hydrocarbon may be used. The aromatic hydrocarbon may be substituted with, for example, alkyl or halide groups. The aliphatic hydrocarbons may suitably be a paraffin which may be linear, branched or cyclic. Suitable hydrocarbon solvents include benzene, toluene, xylene, hexane and cyclohexane. A preferred solvent is benzene. The amount of water employed may suitably be less than about 5% by volume, and preferably from 0.01 to 3% by volume.

The catalyst used in the present invention is cobalt carbonyl. The cobalt carbonyl may be added as such or may be formed under the reaction conditions either during the reaction or in a separate preparative step in the absence of reactants. Thus, the catalyst may be added to the reaction mixture as cobalt metal, suitably in finely divided form, or a cobalt compound, for example a soluble salt such as the nitrate, chloride or acetate. The cobalt carbonyl or cobalt compound is suitably added such that the amount of cobalt is 0.1 to 50%, preferably 1–35%, by weight based on the total weight of mercaptan employed.

The elevated temperature may suitably be in the range from 50° to 300° C., preferably from 150° to 250° C.

The process of the invention may be operated batchwise or continuously, preferably continuously.

The invention will now be further illustrated by reference to the following Examples. However, these Examples should not be construed as limiting the scope of this invention which includes equivalent modifications, variations and embodiments.

EXAMPLE 1

To benzene (30 ml) was added water (2 ml), p-methylbenzyl mercaptan (10 mmol) and dicobalt octacarbonyl (0.5 mmol). The mixture was heated to 185°–190° C. at 850–900 psi carbon monoxide pressure for 24 hours, after which the reaction mixture was filtered and the filtrate concentrated. The product was purified by silica gel chromatography and distillation. p-Xylene was obtained in 84% yield.

EXAMPLE 2

The procedure of Example 1 was repeated except that o-methyl benzyl mercaptan was used in place of p-methylbenzyl mercaptan. o-Xylene was obtained in 48% yield.

EXAMPLE 3

The procedure of Example 1 was repeated except that p-methoxybenzyl mercaptan was used in place of p-methylbenzyl mercaptan. p-Methylanisole was obtained in 58% yield.

EXAMPLE 4

The procedure of Example 1 was repeated except that p-chlorobenzyl mercaptan was used in place of p-methylbenzyl mercaptan. p-Chlorotoluene was obtained in 44% yield.

EXAMPLE 5

The procedure of Example 1 was repeated except that 2,4-dichlorobenzyl mercaptan was used in place of p-methylbenzyl mercaptan. 2,4-Dichloro-toluene was obtained in 63% yield.

EXAMPLE 6

The procedure of Example 1 was repeated except that m-toluenethiol was used in place of p-methylbenzyl mercaptan. Toluene was obtained in 55% yield.

EXAMPLE 7

The procedure of Example 1 was repeated except that p-bromothiophenol was used in place of p-methylbenzyl mercaptan. Bromobenzene was obtained in 77% yield.

EXAMPLE 8

The procedure of Example 1 was repeated except that 2-naphthalene thiol was used in place of p-methylbenzyl mercaptan. Naphthalene was obtained in 91% yield.

We claim:

1. A process for the desulphurisation of a mercaptan of the formula RSH wherein R is a benzylic or aromatic moiety, the process comprising contacting the mercaptan with carbon monoxide at elevated temperature in the presence of an aqueous hydrocarbon solvent and a cobalt carbonyl catalyst.

2. The process of claim 1 wherein the aqueous hydrocarbon contains less than 5% by volume water.

3. The process of claim 1 wherein the amount of cobalt pressure is from 0.1 to 50% by weight based on the total weight of mercaptan employed.

4. The process of claim 1 wherein the mercaptan is a benzylic mercaptan selected from the group p-methylbenzyl mercaptan, o-methylbenzyl mercaptan, p-methoxybenzyl mercaptan, p-chlorobenzyl mercaptan and 2,4-dichlorobenzyl mercaptan.

5. The process of claim 1 wherein the mercaptan is an aromatic mercaptan selected from the group m-toluenethiol, p-bromothiolphenol, 2-naphthalenethiol and phenylthiol.

6. The process of claim 1 wherein the aqueous hydrocarbon contains a hydrocarbon is selected from the group benzene, toluene, xylene, hexene and cyclohexane.

7. The process of claim 1 wherein the temperature is from 50° to 300° C.

* * * * *